United States Patent [19]

Nitta et al.

[11] Patent Number: 4,585,766

[45] Date of Patent: Apr. 29, 1986

[54] 6-OXYGENATED CORTICOID 17α-CARBONATES AND PROCESS FOR PRODUCTION THEREOF

[75] Inventors: Issei Nitta, Machida; Kenichiro Nakao; Motoyoshi Miyake, both of Tokyo; Akira Maruyama, Yokohama; Junko Takashima, Kawasaki, all of Japan

[73] Assignee: Mitsubishi Chemical Industries Ltd., Tokyo, Japan

[21] Appl. No.: 645,099

[22] Filed: Aug. 28, 1984

[30] Foreign Application Priority Data

Sep. 7, 1983 [JP] Japan .................. 58-164772

[51] Int. Cl.$^4$ .............................................. C07J 5/00
[52] U.S. Cl. .................................... 514/180; 514/179; 260/397.45
[58] Field of Search .................... 260/397.45; 514/180

[56] References Cited

U.S. PATENT DOCUMENTS 4,242,334 12/1980 Stache et al. .................. 260/397.45
4,377,575 3/1983 Stache et al. .................. 260/397.45

Primary Examiner—Elbert L. Roberts
Attorney, Agent, or Firm—Oblon, Fisher, Spivak, McClelland & Maier

[57] ABSTRACT

Novel 6-oxygenated corticoid 17α-carbonates are disclosed. These compounds have strong topical anti-inflammatory activity which are accompanied by extremely weak systemic adverse reaction. The present compounds are useful for the treatment of acute and chronic eczema, eczema seborrhoicorum, contact dermatitis, atopic dermatitis, asthma, etc.

11 Claims, No Drawings

6-OXYGENATED CORTICOID 17α-CARBONATES AND PROCESS FOR PRODUCTION THEREOF

BACKGROUND OF THE INVENTION

1. Field of the Invention

This invention relates to novel corticoid derivatives. Corticoid derivatives have anti anti-inflammatory activity and are useful as pharmaceuticals.

2. Description of the Prior Art 6-oxo corticoids are disclosed in Japanese Unexamined Patent Publication No. 73765/79 and corticoid 17α-carbonates are disclosed in Japanese Unexamined Patent Publication No. 36248/79. However, novel derivatives that have more efficacy as pharmaceuticals are always in demand.

The present inventors have synthesized 6-oxo corticoid 17α-carbonate derivatives and found that while these compounds have much stronger topical anti-inflammatory activity the than 6-oxo corticoids, they have only a much weaker thymolytic action (which is an index of systemic side effects) than the corticoid 17α-carbonates. Therefore, the 6-oxo corticoid 17α-carbonate derivatives of this invention are very useful as pharmaceuticals.

SUMMARY OF THE INVENTION

The novel 6-oxo corticoid 17α-carbonate derivatives of the present invention have the formula (I):

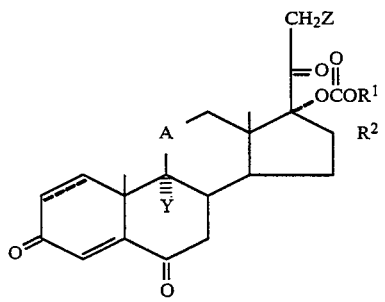

wherein
A is

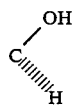

or C=O;
Y is hydrogen or halogen;
Z is a hydroxyl group, halogen atom, a group represented by the following formula (II):

            (II)

wherein $R^3$ is an alkyl group or halogenated alkyl group having 1 to 10 carbon atoms, or a group represented by the following formula (III)

            (III)

wherein $R^4$ is an alkyl group or halogenated alkyl group having 1 to 10 carbon atoms; $R^1$ is an alkyl group having 1 to 10 carbon atoms; $R^2$ is a hydrogen atom or alkyl group having 1 to 10 carbon atoms at the α- or β-position and the bond between $C_1$ and $C_2$ shown by a dotted line is a single or double bond.

The novel derivatives of the present invention may be prepared according to the following methods depending on the definition of Z.

That is the derivatives of the general formula (I) wherein Z is an —OH group, as shown by the general formula (Ia):

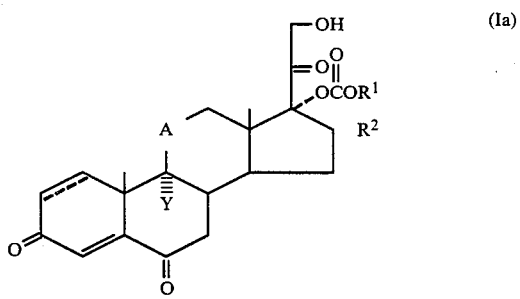

wherein A, Y, $R^1$ and $R^2$ have the same significance as defined in the general formula (I), are prepared by hydrolyzing 6-oxygenated corticoid 17α,21-orthocarbonates represented by the general formula (IV):

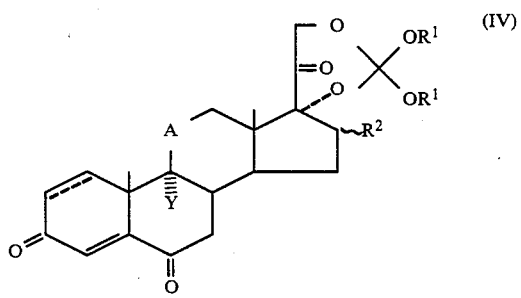

wherein A, Y, $R^1$ and $R^2$ have the same significance as defined in the general formula (I).

The derivatives of the general formula (I) wherein Z is a group —OSO$_2$R$^3$, as shown by the general formula (Ib):

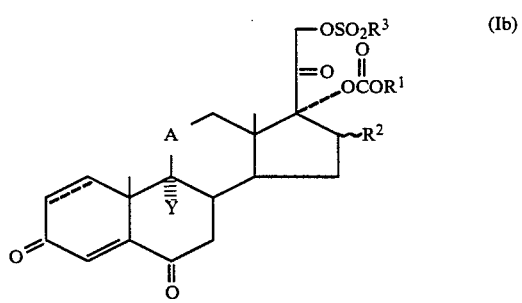

wherein A, Y, $R^1$, $R^2$ and $R^3$ have the same significance as defined in the general formula (I), are prepared by reacting a compound represented by the above formula (Ia) with a sulfonic acid derivative represented by the following formula (IIa) or (IIb):

            (IIa)

            (IIb)

wherein $R^3$ has the same significance as defined in the general formula (II) and $X^1$ is a halogen atom.

The derivatives of the general formula (I) wherein Z is a group —OCOR$^4$, as shown by the general formula (Ic):

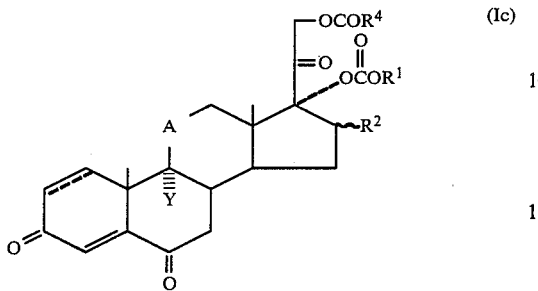

wherein A, Y, $R^1$, $R^2$ and $R^4$ have the same significance as defined in the general formulae (I) and (III), are prepared by reacting a compound represented by the above formula (Ia) with a carboxylic acid derivative represented by the following formula (IIIa) or (IIIb):

wherein $R^4$ has the same significance as defined in the general formula (I) and $X^1$ is a halogen atom.

Further, the derivatives of the general formula (I) wherein Z is a halogen atom, as shown by the general formula (Ie):

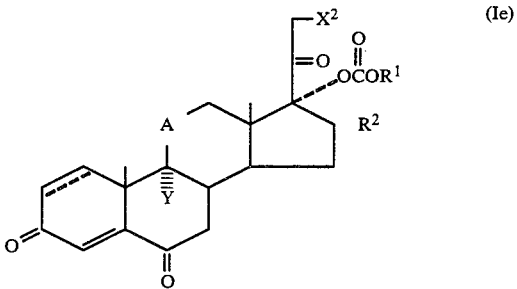

wherein A, Y, $R^1$ and $R^2$ have the same significance as defined in the general formula (I) and $X^2$ is a halogen atom, are prepared by reacting a compound represented by the general formula (Id):

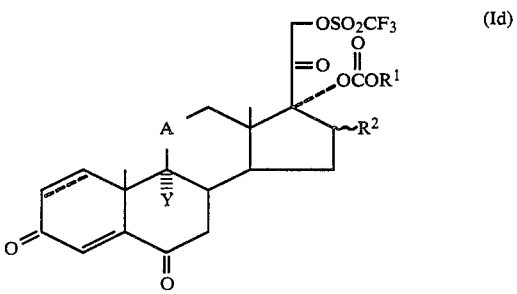

wherein A, Y, $R^1$ and $R^2$ have the same significance as defined in the general formula (I), with a halogen ion-donor.

DETAILED DESCRIPTION OF THE INVENTION

The 6-oxo corticoid 17α-carbonate derivatives of the present invention are represented by the following general formula (I):

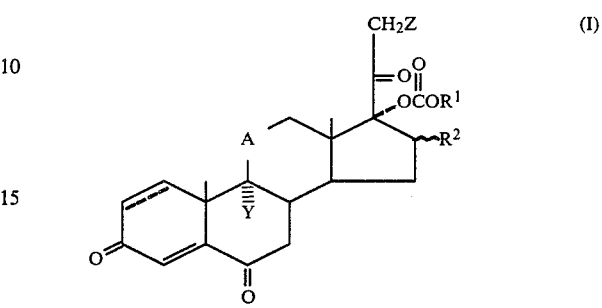

In the above formula, a dotted line represents a single or double bond, A is a group

or C═O, Y is a hydrogen atom or halogen atom such as fluorine, chlorine, bromine, iodine, preferably, fluorine and chlorine and Z is a hydroxyl group; halogen atom such as fluorine, chlorine, bromine and iodine; a group represented by the following formula (II):

wherein $R^3$ is an alkyl group or halogenated alkyl group having 1 to 10 carbon atoms; or a group represented by the following formula (III):

wherein $R^4$ is an alkyl group or halogenated alkyl group having 1 to 10 carbon atoms but a halogen atom is especially preferable. As examples of $R^3$ and $R^4$, alkyl groups having 1 to 10 carbon atoms such as methyl, ethyl, propyl and pentyl groups, etc. and halogenated alkyl groups having 1 to 10 carbon atoms such as trifluoromethyl, fluoromethyl, chloromethyl, chloroethyl and chloropropyl groups, etc. are mentioned.

The substituents: $R^1$ is an alkyl group having 1 to 10 carbon atoms such as methyl, ethyl, propyl, butyl, hexyl and octyl groups, etc. and $R^2$ shows a hydrogen atom or α- or β-alkyl group having 1 to 10 carbon atoms such as methyl, ethyl, propyl and butyl groups, etc., preferably, α-methyl group or β-methyl group.

Specific examples of 6-oxo corticoid 17α-carbonate derivatives include 9α-fluoro-16β-methyl-1,4-pregnadiene-11β,17α,21-triol-3,6,20-trione 17α-methyl carbonate; 9α-fluoro-16β-methyl-1,4-pregnadiene-11β,17α,21-triol-3,6,20-trione 17α-methyl carbonate 21-propionate; 9α-fluoro-16β-methyl-1,4-pregnadiene-11β,17α,21-triol-3,6,20-trione 17α-methyl carbonate 21-trifluoromethane-sulfonate; 21-chloro-9α-fluoro-16β-methyl-1,4-pregnadiene-11β,17α-diol-3,6,20-trione 17α-methyl carbonate; 9α-fluoro-16β-methyl-1,4-pregnadiene-11β,17α,21-triol-3,6,20-trione 17α-ethyl carbonate; 9α-fluoro-16α-methyl-1,4-pregnadiene-11β,17α,21-triol- 3,6,20-trione 17α-methyl carbonate; 9α-fluoro-16β-methyl-4-pregnene-11β,17α,21-triol-3,6,20-trione 17α-methyl carbonate; 21-chloro-9α-fluoro-16β-methyl-1,4-pregnadiene-11β,17α-diol-3,6,20-trione 17α-ethyl carbonate; 9α-fluoro-16β-methyl-1,4-pregnadiene-11β,17α,21-triol-3,6,20-trione 17α-propyl carbonate; 21-chloro-9α-fluoro-16β-methyl-1,4-pregnadiene-11β,17α-diol-3,6,20-trione 17α-propyl carbonate; 21-chloro-9α-fluoro-16α-methyl-1,4-pregnadiene-11β,17α-diol-3,6,20-trione 17α-methyl carbonate; 21-chloro-9α-fluoro-16β-methyl-4-pregnene-17α-ol-3,6,11,20-tetraone 17α-methyl carbonate; 21-chloro-9α-fluoro-16β-methyl-1,4-pregnadiene-17α-ol-3,6,11,20-tetraone 17α-ethyl carbonate; 9α,21-dichloro-16β-methyl-1,4-pregnadiene-11β,17α-diol-3,6,20-trione 17α-methyl carbonate; 9α-fluoro-16β-methyl-pregna-1,4-diene-11β,17α,21-triol-3,6,20-trione 17α-methyl carbonate 21-methanesulfonate; 9α-fluoro-16β-methyl-pregna-1,4-diene-11β,17α,21-triol-3,6,20-trione 17α-methyl carbonate 21-chlorobutylate; 9α-fluoro-21-chloro-pregna-1,4-diene-11β,17α-diol-3,6,21-trione 17α-ethyl carbonate; 9α,21-difluoro-16β-methyl-1,4-pregnadiene-11β,17α-diol-3,6,20-trione 17α-ethyl carbonate and 9α-fluoro-21-iodo-16β-methyl-1,4-pregnadiene-11β,17α-diol-3,6,20-trione 17α-ethyl carbonate, and the 21-halogenated derivatives such as 21-chloro-9α-fluoro-16β-methyl-1,4-pregnadiene-11β,17α-diol-3,6,20-trione 17α-methyl carbonate; 21-chloro-9α-fluoro-16β-methyl-1,4-pregnadiene-11β,17α-diol-3,6,20-trione 17α-ethyl carbonate; 21-chloro-9α-fluoro-16β-methyl-1,4-pregnadiene-11β,17α-diol-3,6,20-trione 17α-propyl carbonate; 21-chloro-9α-fluoro-16α-methyl-1,4-pregnadiene-11β,17α-diol-3,6,20-trione 17α-methyl carbonate; 9α,21-difluoro-16β-methyl-1,4-pregnadiene-11β,17α-diol-3,6,20-trione 17α-methyl carbonate, etc. are especially preferable since they have considerably high topical anti-inflammatory activity.

The preparation of the compounds of the present invention is described according to the definition of Z of the general formula (I), as follows:

(A) The derivatives of the general formula (I) wherein Z is a hydroxy group, i.e. 17α-carbonate derivatives represented by the following general formula (Ia):

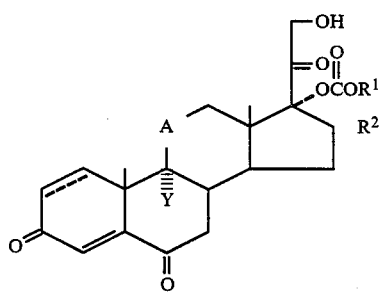

(Ia)

wherein A, Y, $R^1$ and $R^2$ have the same significance as defined in the general formula (I).

These derivatives are prepared by hydrolysis under acidic conditions using a 6-oxo corticoid 17α,21-dialkyl orthocarbonate of the formula (IV) as a starting material, which is prepared by reacting a 6-oxo corticoid of the formula (V) disclosed in Japanese Unexamined Patent Publication No. 73765/79 with the corresponding alkyl orthocarbonate under acidic conditions as shown in the following reaction scheme:

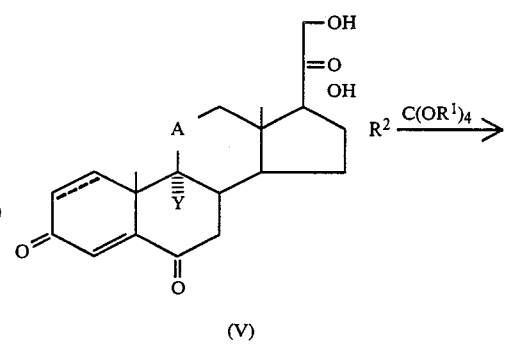

(V)

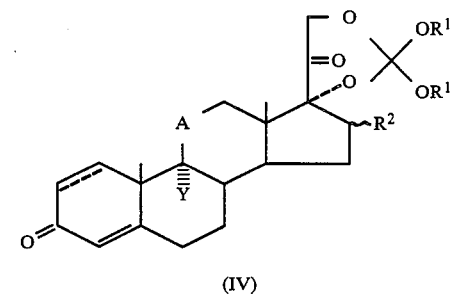

(IV)

wherein A, Y, $R^1$ and $R^2$ have the same significance as defined in the general formula (I).

In the above hydrolyzing reaction, usually, organic carboxylic acids such as acetic acid, propionic acid, valeric acid, etc., organic sulfonic acids such as p-toluenesulfonic acid, benzenesulfonic acid, etc. and inorganic acids such as hydrochloric acid, sulfuric acid, etc. are used. However, in this case, 21-carbonates are formed as by-products simultaneously with the desired 17α-carbonates of the formula (Ia). Therefore, in order to suppress by-production of 21-carbonates, it is preferable to maintain the pH of the reaction mixture at 5 to 6 by adding alkali metal salts of organic acids such as sodium acetate, potassium propionate, etc. in addition to organic carboxylic acids such as acetic acid, propionic acid, etc., or to employ Lewis acids such as aluminum chloride, zinc chloride, etc. but the employment of Lewis acids is more preferable.

Where Lewis acids are employed, aqueous alcohols or aqueous cyclic ethers such as aqueous tetrahydrofuran, aqueous dioxane, etc. are used as a solvent and preferably aqueous alcohols are used. As such alcohols, those represented by the general formula: $R^1OH$ wherein $R^1$ has the same significance as defined in the generl formula (I) are desired. Use of other alcohols is undesirable since it is probable to induce transesterification reaction resulting in the contamination of the reaction product. Content of water in the alcohol is normally 5 to 40 weight %. The reaction temperature is 0° to 50° C. and the reaction period is 0.5 to 4 hours.

(B) The derivatives of the general formula (I) wherein Z is a group —$OSO_2R^3$, i.e. 21-sulfonic acid ester derivatives of the following general formula (Ib):

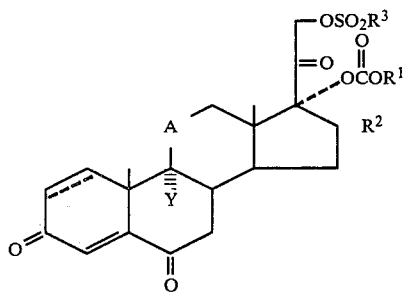

(Ib)

wherein A, Y, $R^1$, $R^2$ and $R^3$ have the same significance as defined in the general formula (I).

These derivatives are prepared by reacting 17α-carbonate derivatives of the formula (Ia) obtained in (A) above with sulfonic acid anhydride or sulfonic acid halide represented by the general formula (IIa) or (IIb):

  (IIa)

  (IIb)

wherein $R^3$ has the same significance as defined in the general formula (II) and $X^1$ is a halogen atom.

Such sulfonic acid derivatives include, for example, methanesulfonyl chloride, p-toluenesulfonyl chloride, trifluoromethanesulfonyl chloride, trifluoromethanesulfonic acid anhydride, etc. The amount to be used is 1 to 3 mols per one mol of 17α-carbonate derivatives of the formula (Ia).

As the solvent, aromatic amines such as pyridine are used, which may be diluted with halogenated hydrocarbons such as methylene chloride, dichloroethane, etc.

The reaction temperature is from a room temperature to −40° C. and the reaction period is from 5 minutes to 2 hours.

(C) The derivatives of the general formula (I) wherein Z is a group —OCOR$^4$, i.e. 21-carboxylic acid ester derivatives of the general formula (Ic):

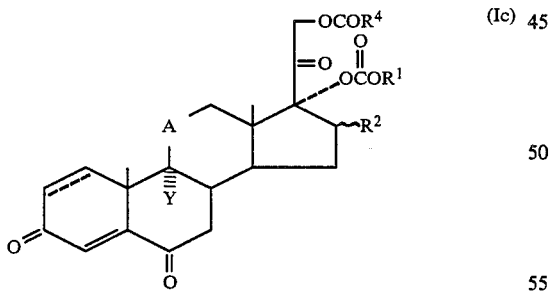

(Ic)

wherein A, Y, $R^1$, $R^2$ and $R^4$ have the same significance as defined in the general formula (I).

These derivatives are prepared by reacting 17α-carbonate derivatives of the formula (Ia) obtained in (A) above, with carboxylic acid anhydride or carboxylic acid halide represented by the general formula (IIIa) or (IIIb):

  (IIIa)

  (IIIb)

wherein $R^4$ has the same significance as defined in the general formula (III) and $X^1$ is a halogen atom.

As the carboxylic acid derivatives, for example, acetic acid anhydride, propionic acid anhydride, butyryl chloride and cyclopropyl carbonyl chloride are mentioned. The amount to be used is 1 to 3 mols per 1 mol of 17α-carbonate derivatives of the general formula (Ia).

As the solvent, aromatic amines such as pyridine are used, which may be diluted with halogenated hydrocarbons such as methylene chloride, dichloroethane, etc.

The reaction temperature is from −30° C. to 50° C. and the reaction period is from 10 minutes to 3 hours.

(D) The derivatives of the general formula (I) wherein Z is a halogen atom, i.e. 21-halogenated corticoid derivatives represented by the general formula (Id):

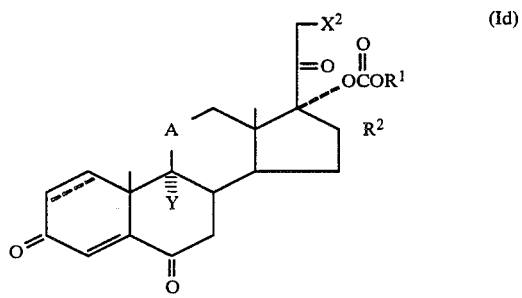

(Id)

wherein A, Y, $R^1$ and $R^2$ have the same significance as defined in the general formula (I) and $X^2$ is a halogen atom.

The derivatives are prepared by reacting 21-trifluoromethane sulfonate derivative of the general formula (Ib'):

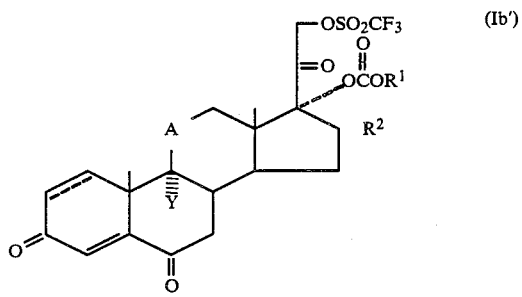

(Ib')

wherein A, Y, $R^1$ and $R^2$ have the same significance as defined in the general formula (I), prepared according to the method described in the (B) above with a halogen ion-donor.

As the halogen ion-donor, lithium chloride, lithium bromide, lithium iodide, potassium chloride, etc. may be mentioned. Where 21-sulfonates are those other than trifluoromethane sulfonate, such as methane sulfonate, p-toluenesulfonate, etc. severer reaction conditions are required since they are not reactive, and such severe conditions may cause the decomposition of the desired product resulting in considerably low yield thereof. Thus, the use of such 21-sulfonates is not preferred.

The amount of the halogen ion-donor to be used is 1 to 3 mols per 1 mol of 21-trifluoromethane sulfonate derivative of the formula (Ib').

The reaction is carried out in an aprotic solvent such as dimethylformamide, dimethylacetamide, dimethylsulfoxide, etc. at a temperature of 0° to 40° C., preferably, at a room temperature. Usually, the reaction period is 0.5 to 3 hours.

The thus obtained 6-oxo corticoid 17α-carbonate derivatives of the formula (I) can be purified by re-crystallization, etc.

The 6-oxo corticoid 17α-carbonate derivatives of the formula (I) have strong topical anti-inflammatory activity and are very useful as anti-inflammatory agents having week systemic side effects, particularly as topical anti-inflammatory agents. They can be used for the treatment of acute and chronic eczema, eczema seborrhoicorum, contact eczema, atopic dermatitis, psoriasis, etc. The derivatives of the present invention may be formulated into a preparation suuitable for topical administration in conventional manner with the aid of one or more carriers or excipients. Examples of types of preparation include ointments, lotions, creams, sprays, powders, drops (e.g., ear drips and eye drops), suppositories or retention enemas (e.g., for the treatmen of rectal or colonic inflammations) and tablets or pellets (e.g., for the treatment of aphthous ulcers) and aerosols.

The proportion of active steroid in the compositions according to the invention depends on the precise type of formulations to be prepared but will generally be within the range of from 0.0001% to 5% by weight. Generally, however, for most types of preparations advantageously the proportion used will be within the range of from 0.001 to 0.5% and preferably 0.01 to 0.25%.

The present invention while explained in more detail referring to the examples but is clearly not limited to the following examples.

EXAMPLES

Preparation of the Starting Material

Synthesis of 9α-fluoro-16β-methyl-1,4-pregnadiene-11β,17α,21-triol-3,6,20-trione 17α,21-dimethyl orthocarbonate To 1.0 g of 9α-fluoro-16β-methyl-1,4-pregnadiene-11β,17α,21-triol-3,6,20-trione are added 20 ml of tetrahydrofuran, 1.0 ml of methyl orthocarbonate and 0.04 g of p-toluenesulfonic acid, and the mixture is stirred at room temperature for 3 hours.

The resulting reaction mixture is poured into iced water containing sodium bicarbonate and an extraction is carried out with ethyl acetate. The organic layer is washed with water and dried. After the solvent is removed by distillation, about 1 g of yellow crystals are obtained.

The yellow crystals are dissolved in 5 ml of chloroform and passed through a column packed with 40 g of silica gel. Elution is then carried out with chloroform-ethyl acetate (2:1) and the solvent is removed from the eluate by distillation. As the result, 1.22 g of 9α-fluoro-16β-methyl-1,4-pregnadiene-11β,17α,21-triol-3,6,20-trione 17α,21-dimethyl orthocarbonate is obtained. Analysis by thin layer chromatography [silica gel 0.25 mm, chloroform-ethyl acetate (2:1)] reveals one spot. The product is used as a starting material for the next step without further purification.

When ethyl orthocarbonate and propyl orthocarbonate are reacted respectively in the same manner in place of methyl orthocarbonate, 9α-fluoro-16β-methyl-1,4-pregnadiene-11β,17α,21-triol-3,6,20-trione 17α,21-diethyl orthocarbonate and 9α-fluoro-16β-methyl-1,4-pregnadiene-11β,17α,21-triol-3,6,20-trione 17α,21-dipropyl orthocarbonate are obtained.

EXAMPLE 1

9α-fluoro-16β-methyl-1,4-pregnadiene-11β,17α,21-triol-3,6,20-trione 17α-methyl carbonate 1.0 g (2.09 m mols) of 9α-fluoro-16β-methyl-1,4-pregnadiene-11β,17α,21-triol-3,6,20-trione 17α,21-dimethyl orthocarbonate is added to a solution mixture of 123 ml of methanol and 50 ml of 0.56% aqueous solution of aluminum chloride. The mixture is stirred at 40° C. for one hour. The resulting reaction mixture is poured into 600 ml of saturated saline solution. Extraction is carried out with ethyl acetate and the solvent is removed by distillation. As the result, 1.13 g of an oily matter is obtained.

The oily matter is charged in the column packed with 40 g of silica gel and eluted with 2% methanol-dichloroethane. After the solvent is removed from the eluate by distillation, 0.71 g of 9α-fluoro-16β-methyl-1,4-pregnadiene-11β,17α,21-triol-3,6,20-trione 17α-methylcarbonate are obtained.

Melting point: 160°–162° C.

EXAMPLE 2

21-chloro-9α-fluoro-16β-methyl-1,4-pregnadiene-11β,17α-diol-3,6,20-trione 17α-methyl carbonate 0.75 ml of pyridine and 20 ml of methylene chloride are added to 0.54 g (1.16 m mols) of 9α-fluoro-16β-methyl-1,4-pregnadiene-11β,17α,21-triol-3,6,20-trione 17α-methyl carbonate and the mixture is cooled at −20° C.

0.35 ml (2.08 m mols) of trifluoromethane sulfonic acid anhydride are added thereto and the mixture is stirred for 30 minutes. The resulting reaction mixture is poured into 50 ml of ice water containing 1 ml of hydrochloric acid and the hydrochloric acid layer is separated, which is washed successively with 5% aqueous solution of hydrochloric acid, 5% aqueous solution of sodium bicarbonate and saturated saline solution and dried.

The thus obtained methylene chloride solution is concentrated and 3.5 g of a solution of 9α-fluoro-16β-methyl-1,4-pregnadiene-11β,17α,21-triol-3,6,20-trione 17α-methyl carbonate 21-trifluoromethane sulfonate in methylene chloride are obtained.

To the solution are added 7.5 ml of dimethylformamide and 0.5 g of lithium chloride, and the mixture is stirred at room temperature for 40 minutes. The reaction solution is poured into 50 ml of ice water, and extraction is carried out with 50 ml of methylene chloride. The extract is concentrated to give 0.62 g of an oily matter.

The oily matter is charged in a column packed with 25 g of silica gel and eluted with benzene-ethyl acetate (2:1). After the solvent is removed by distillation, 0.54 g of 21-chloro-9α-fluoro-16β-methyl-1,4-pregnadiene-11β,17α-diol-3,6,20-trione 17α-methyl carbonate are obtained. The product is recrystallized from ethyl acetate-n-hexane.

Melting point: 185°–165° C.

Elementary analysis: Found(%): C, 59.35; H, 5.98. Calcd. (%) for $C_{24}H_{28}O_7ClF$: C, 59.69; H, 5.84.

EXAMPLE 3

9α-fluoro-16β-methyl-1,4-pregnadiene-11β,17α,21-triol-3,6,20-trione 17α-ethyl carbonate 1.1 g of 9α-fluoro-16β-methyl-1,4-pregnadiene-11β,17α,21-triol-3,6,20-trione 17α,21-diethyl orthocarbonate are added to a mixture of 123 ml of ethanol and 50 ml of 0.56% aqueous solution of aluminum chloride, and the mixture is stirred at 40° C. for one hour. The reaction mixture is treated in the same manner as described in Example 1. After carrying out column chromatography, 0.79 g of 9α-fluoro-16β-methyl-1,4-pregnadiene-11β,17α,21-triol-3,6,20-trione 17α-ethyl carbonate are obtained.

Melting point: 130°–133° C.

EXAMPLE 4

21-chloro-9α-fluoro-16β-methyl-1,4-pregnadiene-11β,17α-diol-3,6,20-trione 17α-ethyl carbonate To 0.60 g of 9α-fluoro-16β-methyl-1,4-pregnadiene-11β,17α,21-triol-3,6,20-trione 17α-ethyl carbonate are added 0.75 ml of pyridine and 20 ml of methylene chloride, and the mixture is cooled to −20° C. 0.35 ml of trifluoromethane sulfonic acid anhydride are added thereto and stirred for 25 minutes. The reaction mixture is treated in the same manner as described in Example 2 and 4 g of a solution of 9α-fluoro-16β-methyl-1,4-pregnadiene-11β,17α,21-triol-3,6,20-trione 17α-ethyl carbonate 21-trifluoromethane sulfonate in methylene chloride are obtained.

To the solution, 7.5 ml of dimethylformamide and 0.5 g of lithium chloride are added and stirred at room temperature for one hour. Thereafter, the procedure described in Example 2 is followed. After carrying out column chromatography, 0.6 g of 21-chloro-9α-fluoro-16β-methyl-1,4-pregnadiene-11β,17α-diol-3,6,20-trione 17α-ethyl carbonate are obtained. The product is recrystallized from benzen-n-hexane.

Melting point: 202° C. (decomposition).
Elementary analysis: Found (%): C, 60.65; H, 6.12. Calcd. (%) for $C_{25}H_{30}O_7ClF$: C, 60.42; H, 6.08.

EXAMPLE 5

9α-fluoro-16β-methyl-1,4-pregnadiene-11β,17α,21-triol-3,6,20-trione 17α-propyl carbonate 1.67 g of 9α-fluoro-16β-methyl-1,4-pregnadiene-11β,17α,21-triol-3,6,20-trione 17α,21-dipropyl orthocarbonate are added to 187 ml of n-propanol and 80 ml of 0.56% aqueous solution of aluminum chloride, and the mixture is stirred at 40° C. for one hour. The reaction mixture is treated in the same manner as described in Example 1. After carrying out column chromatography, 0.86 g of 9α-fluoro-16β-methyl-1,4-pregnadiene-11β,17α,21-triol-3,6,20-trione 17α-propyl carbonate are obtained.

Melting point: 197°–200° C. (decomposition).

EXAMPLE 6

21-chloro-9α-fluoro-16β-methyl-1,4-pregnadiene-11β,17α-diol-3,6,20-trione 17α-propyl carbonate To 0.70 g of 9α-fluoro-16β-methyl-1,4-pregnadiene-11β,17α,21-triol-3,6,20-trione 17α-propyl carbonate are added 0.75 ml of pyridine and 20 ml of methylene chloride, and the mixture is cooled to −20° C. 0.35 ml of trifluoromethane sulfonic acid anhydride are added thereto, and the mixture is stirred for 25 minutes. The reaction mixture is treated in the same manner as described in Example 2 and 2.7 g of a solution of 9α-fluoro-16β-methyl-1,4-pregnadiene-11β,17α,21-triol-3,6,20-trione 17α-propyl carbonate 21-trifluoromethane sulfonate in methylene chloride is obtained.

7.5 ml of dimethylformamide and 0.5 g of lithium chloride are added to the solution and the mixture is stirred at room temperature for one hour. Thereafter, the procedure described in Example 2 is followed. After carrying out column chromatography, 0.45 g of 21-chloro-9α-fluoro-16β-methyl-1,4-pregnadiene-11β,17α-diol-3,6,20-trione 17α-propyl carbonate are obtained. The product is recrystallized from ethyl acetate-n-hexane.

Melting point: 200°–202° C. (decomposition).

EXAMPLE 7

9α-fluoro-16α-methyl-1,4-pregnadiene-11β,17α,21-triol-3,6,20-trione 17α-methyl carbonate 1.3 g of 9α-fluoro-16α-methyl-1,4-pregnadiene-11β,17α,21-triol-3,6,20-trione 17α,21-dimethyl orthocarbonate are added to a mixture solution of 30 ml of methanol, 21 ml of tetrahydrofuran and 5 ml of 0.56% aqueous solution of aluminum chloride, and the mixture is stirred at 40° C. for 1.5 hours. The reaction mixture is treated in the same manner as described in Example 1. After carrying out column chromatography, 0.97 g of 9α-fluoro-16α-methyl-1,4-pregnadiene-11β,17α,21-triol-3,6,20-trione 17α-methyl carbonate are obtained.

Melting point: 248°–251° C. (decomposition).

EXAMPLE 8

21-chloro-9α-fluoro-16α-methyl-1,4-pregnadiene-11β,17α-diol-3,6,20-trione 17α-methyl carbonate To 0.6 g (1.29 m mols) of 9α-fluoro-16α-methyl-1,4-pregnadiene-11β,17α,21-triol-3,6,20-trione 17α-methyl carbonate are added 0.73 ml of pyridine and 20 ml of methylene chloride, and the mixture is cooled to −20° C. 0.34 ml (2.02 m mols) of trifluoromethane sulfonic acid anhydride are added thereto and the mixture is stirred for 30 minutes. The reaction mixture is treated in the same manner as described in Example 2 and 3 g of a solution of 9α-fluoro-16α-methyl-1,4-pregnadiene-11β,17α,21-triol-3,6,20-trione 17α-methyl carbonate 21-trifluoromethane sulfonate in methylene chloride are obtained.

7.5 ml of dimethylformamide and 0.5 g of lithium chloride are added to the solution, and the mixture is stirred at room temperature for one hour. Thereafter, the procedure described in Example 2 is followed. After carrying out column chromatography, 0.41 g of 21-chloro-9α-fluoro-16α-methyl-1,4-pregnadiene-11β,17α-diol-3,6,20-trione 17α-methyl carbonate are obtained. The product is recrystallized form ethyl acetate-n-hexane.

Melting point: 268°–271° C. (decomposition).
Elementary analysis: Found (%): C, 59.64; H, 5.96. Calcd. (%) for $C_{24}H_{28}O_7ClF$: C, 59.68; H, 5.85.

REFERENCE EXAMPLE 1

21-chloro-9α-fluoro-16β-methyl-1,4-pregnadiene-11β,17α-diol-3,6,20-trione 17α-propionate To 0.285 g of 9α-fluoro-16β-methyl-1,4-pregnadiene-11β,17α,21-triol-3,6,20-trione 17α-propionate are added 3 ml of pyridine and 0.06 ml of methane sulfonylchloride and the mixture is stirred at room temperature for 30 minutes.

The resulting reaction mixture is subjected to extraction with methylene chloride and extract is successively washed with 5% HCl, aqueous sodium bicarbonate solution and aqueous saline solution. After drying, methylene chloride is removed by distillation to obtain 9α-fluoro-16β-methyl-1,4-pregnadiene-11β,17α,21-triol-3,6,20-trione 17α-propionate 21-methane sulfonate.

3 ml of dimethylformamide and 0.3 g of lithium chloride are added thereto and the mixture is stirred at 80° C. for 8 hours. The reaction mixture is poured to a large volume of water and the crystals formed are separated by filtration. After drying, the crystals are dissolved in 2 ml of benzene, passed through a column packed with silica gel and eluted with ethyl acetate-benzene (5:95). After removing the solvent by distillation, 0.220 g of 21-chloro-9α-fluoro-16β-methyl-1,4-pregnadiene-11β,17α-diol-3,6,20-trione 17α-propionate are obtained. The product is crystallized from ethyl acetate.

Melting point: 228.5° C. (decomposition).

REFERENCE EXAMPLE 2

21-chloro-9α-fluoro-16β-methyl-1,4-pregnadiene-11β,17α-diol-3,20-dione 17α-methyl carbonate To 0.50 g of 9α-fluoro-16β-methyl-1,4-pregnadiene-11β,17α,21-triol-3,20-dione 17α-methyl carbonate are added 20 ml of methylene chloride, 0.75 ml of pyridine and 0.35 ml of trifluoromethane sulfonic acid anhydride and the mixture is stirred at −20° C. for 1.5 hours. The reaction mixture is treated in the same manner as described in Example 2 and 5 ml of a solution of 9α-fluoro-16β-methyl-1,4-pregnadiene-11β,17α,21-triol-3,20-dione 17α-methyl carbonate 21-trifluoromethane sulfonate in methylene chloride are obtained.

7.5 ml of dimethylformamide and 0.5 g of lithium chloride are added to the solution and the mixture is stirred at room temperature for 1.5 hours. Thereafter, the procedure described in Example 2 is followed. After carrying out column chromatography, 0.532 g of 21-chloro-9α-fluoro-16β-methyl-1,4-pregnadiene-11β,17α-diol-3,20-dione 17α-methyl carbonate are obtained. The product is recrystallized from ethyl acetate.

Melting point: 196°–198° C. (decomposition).

EXPERIMENTAL EXAMPLE

Method

Experiments are conducted, according to the following procedures, on topical anti-inflammatory activity and on thymolytic action which is an index of systemic side effects, for the purpose of clarifying pharmacological activities of the compounds of the present invention.

(1) Experiment on topical anti-inflammatory activity

Male mice of ddY-strain having a body weight of 15–20 g are divided at random into groups, each consisting of 10 mice.

0.9% sodium chloride, 0.4% Tween 80, 0.5% carboxymethyl cellulose and 0.9% benzyl alcohol are dissolved or suspended in distilled water, which is used as a suspending medium.

The compounds to be tested are dissolved in a mixture of the suspending medium:pyridine:diethyl ether=1:4:5 and mixed with equal volume of diethyl ether containing 10% croton oil and the mixture is used as the test liquid.

Commercially available felt having a thickness of 5 mm is cut in 7 mm×7 mm square and adhered to ring tweezers using alkyl-α-cyanoacrylate. The felt is soaked in the test liquid and the liquid is applied to a right ear of the mouse by rubbing it with the felt at a fixed pressure without anesthesia. The left ear is left untreated. At 5th hours after application, mice are killed and both of the ears are cut and weighed. The rate (%) of increase in the weight of right ear against that of left ear is calculated as the edema ratio. Edema ratios obtained on the test compounds are compared with those obtained on control and edema-repressing rate is obtained.

(2) Experiment on thymolytic action

Male rats of Wistar strain having a body weight of 120–150 g are divided at random into groups, each consisting of 8 rats.

The compounds to be tested are dissolved in a liquid consisting of croton oil:cotton seed oil:ethanol=1:89:10 and the solution is used for injection.

The rats are anesthesized by inhalation of ether and 20 ml of air are subcutaneously injected into hypodermic organ at the back of the rats using a thin injection needle to form an oval-shaped air cavity. After the rats recovered from anesthesia, they are kept on normal food and water. At 8th days after injection, rats are killed by depletion and dissected. The thymus gland is taken out and the wet weight is measured. Thymus weights obtained on the test compounds are divided with those obtained on control, and thymus gland atrophy rate is obtained.

Results

In each of the experiments on anti-inflammatory activity and thymolytic action, clobetasol 17-propionate and betamethasone 17,21-dipropionate are used as standard compounds and anti-inflammatory activity ratio and thymolytic activity ratio against clobetasol 17-propionate are calculated using linear regression parallel test method.

The results are shown in Table 1 below. In the Table, the compounds are indicated by relevant Example numbers or Reference Example numbers.

TABLE 1

| Compounds | Anti-inflammatory activity ratio (A) | Thymolytic activity ratio (B) | R = A/B |
|---|---|---|---|
| Clobetasol 17-propionate | 1 | 1 | 1 |
| Example 2 | 3.0 | 0.018 | 167 |
| Example 4 | 1.3 | 0.048 | 27 |
| Example 6 | 0.74 | 0.24 | 3.1 |
| Example 8 | 0.51 | 0.092 | 5.5 |
| Reference Example 1 | 0.53 | 0.29 | 1.8 |
| Reference Example 2 | 0.96 | 1.2 | 0.8 |
| Betamethasone 17,21-dipropionate | 0.080 | 0.030 | 2.7 |

As is apparent from the above Table 1, the compounds of the present invention show an anti-inflammatory activity comparable to or better than that of clobetasol 17-propionate.

With respect to thymolytic action, all the compounds of the present invention have weaker action than clobetasol 17-propionate.

Thus, since the present compounds have very weak systemic side effects and strong topical anti-inflammatory activity, it is obvious that they are useful compounds.

What is claimed is:

1. A 6-oxygenated corticoid 17α-carbonate of the formula (I):

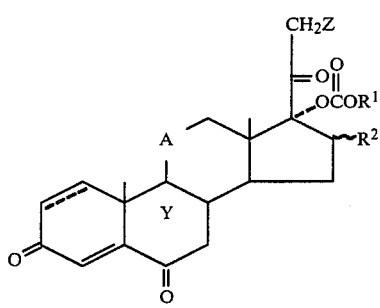

wherein
A is

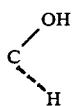

or —C=O;
Y is hydrogen or halogen;
Z is hydroxyl, halogen, a group of the formula (II);

—OSO$_2$R$^3$  (II)

wherein R$^3$ is alkyl or halogenated alkyl having 1 to 10 carbon atoms, or a group of the formula (III):

—OCOR$^4$  (III)

wherein R$^4$ is alkyl or halogenated alkyl having 1 to 10 carbon atoms;
R$^1$ is C$_1$–C$_{10}$ alkyl;
R$^2$ is hydrogen or C$_1$–C$_{10}$ alkyl at the α- or β-position; and
the bond between C$_1$ and C$_2$ shown by a dotted line is a single or double bond.

2. The compound of claim 1 being 9α-Fluoro-16β-methyl-1,4-pregnadiene-11β,17α,21-triol-3,6,20-trione 17α-methyl carbonate.

3. The compound of claim 1 being 21-Chloro-9α-fluoro-16β-methyl-1,4-pregnadiene-11β,17α,diol-3,6,20-trione 17α-methyl carbonate.

4. The compound of claim 1 being 9α-Fluoro-16β-methyl-1,4-pregnadiene-11β,17α,21-triol-3,6,20-trione 17α-ethyl carbonate.

5. The compound of claim 1 being 21-Chloro-9α-fluoro-16β-methyl-1,4-pregnadiene-11β,17α-diol-3,6,20-trione 17α-ethyl carbonate.

6. The compound of claim 1 being 9α-Fluoro-16β-methyl-1,4-pregnadiene-11β,17α,21-triol-3,6,20-trione 17α-propyl carbonate.

7. The compound of claim 1 being 21-Chloro-9α-fluoro-16β-methyl-1,4-pregnadiene-11β,17α-diol-3,6,20-trione 17α-propyl carbonate.

8. The compound of claim 1 being 9α-Fluoro-16α-methyl-1,4-pregnadiene-11β,17α,21-triol-3,6,20-trione 17α-methyl carbonate.

9. The compound of claim 1 being 21-Chloro-9α-fluoro-16α-methyl-1,4-pregnadiene-11β,17α-diol-3,6,20-trione 17α-methyl carbonate.

10. A process for producing a 6-oxygenated corticoid 17α-carbonate of the formula (Ie):

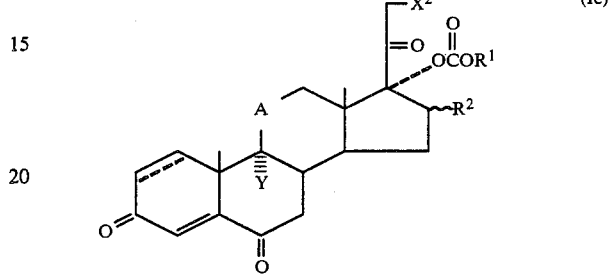

wherein:
A is

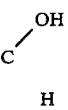

or C=O;
Y is hydrogen or halogen;
R$^1$ is C$_1$–C$_{10}$ alkyl;
R$^2$ is hydrogen or C$_1$–C$_{10}$ alkyl at the α- or β-position;
X$^2$ is halogen; and
the bond between C$_1$ and C$_2$ shown by the dotted line is a single or double bond, comprising:
(a) reacting a compound of the formula (Id):

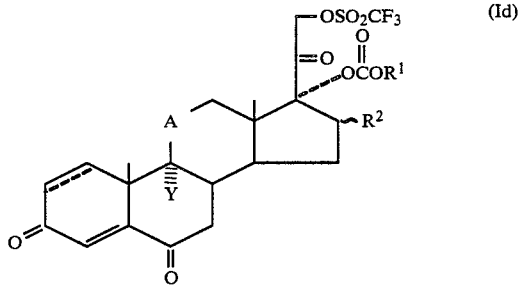

wherein A, Y, R$^1$ and R$^2$ are as defined in the formula (Ie), with a halogen ion-releasing reagent.

11. A pharmaceutical composition comprising
(a) an effective amount of the compound of claim 1, and
(b) a pharmaceutically acceptable carrier.

* * * * *